(12) United States Patent
Matsumoto et al.

(10) Patent No.: US 7,863,248 B2
(45) Date of Patent: Jan. 4, 2011

(54) TYROSINASE ACTIVITY INHIBITOR AND AMELIORANT FOR FACIAL BLOOD FLOW

(75) Inventors: Hitoshi Matsumoto, Saitama (JP); Yuko Nakamura, Saitama (JP); Megumi Yamagishi, Saitama (JP); Kyoko Ito, Saitama (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 278 days.

(21) Appl. No.: 10/577,135

(22) PCT Filed: Oct. 20, 2004

(86) PCT No.: PCT/JP2004/015470

§ 371 (c)(1),
(2), (4) Date: Apr. 25, 2006

(87) PCT Pub. No.: WO2005/042555

PCT Pub. Date: May 12, 2005

(65) Prior Publication Data

US 2007/0082024 A1    Apr. 12, 2007

(30) Foreign Application Priority Data

Oct. 30, 2003    (JP) ............................. 2003-371080

(51) Int. Cl.
*A61K 31/70* (2006.01)
(52) U.S. Cl. .............................. 514/27; 536/8; 536/18.1
(58) Field of Classification Search ........................ None
See application file for complete search history.

(56) References Cited

U.S. PATENT DOCUMENTS

| 5,670,154 | A   |   | 9/1997 | Hara et al. |
| 6,767,999 | B2  | * | 7/2004 | Smirnov et al. ............ 536/18.5 |

FOREIGN PATENT DOCUMENTS

| EP | 1208755 | | 5/2002 |
| FR | 2723316 | A | 2/1996 |
| JP | A2-62-048611 | | 3/1987 |
| JP | A-62-077328 | | 4/1987 |
| JP | 11-255637 | | 9/1999 |
| JP | 2002-029980 | | 1/2002 |
| JP | 2002-053468 | | 2/2002 |
| JP | 2002-068993 | | 3/2002 |
| JP | 2002-128689 | | 5/2002 |
| JP | 2003-277271 | | 10/2003 |
| JP | 2004-107245 | | 4/2004 |
| JP | 2004-262878 | | 9/2004 |
| WO | WO 01/01798 | A1 | 1/2001 |
| WO | WO 01/52809 | A | 7/2001 |
| WO | WO 03/053336 | | 7/2003 |

OTHER PUBLICATIONS

Office Action dated Feb. 9, 2009 in corresponding Canadian patent application No. 2,543,676.
A. Colantuoni, et al. "Effects of Vaccinium Myrtillus Anthocyanosides on Arterial Vasomotion," *Arzneimittel Forschung. Drug Research*, vol. 41, No. 9, Sep. 1, 1991, pp. 905-909.
"Le raisin", *Journal de Pediatrie et de Puericulture*, vol. 11, No. 7, Oct. 1, 1998, p. 444.
Official Communication issued from the European Patent Office on May 14, 2009 for the corresponding European patent application No. 04792636.5.
Office Action issued on Nov. 4, 2009 in corresponding Japanese patent application No. 2005-515111.
Official Communication issued from the Canadian Intellectual Property Office on Apr. 13, 2010 for the corresponding Canadian patent application No. 2,543,676.

* cited by examiner

*Primary Examiner*—Elli Peselev
(74) *Attorney, Agent, or Firm*—Posz Law Group, PLC

(57) ABSTRACT

A tyrosinase activity inhibitor and an ameliorant for facial blood flow that are excellent in terms of safety, and medicinal compositions, food compositions, and cosmetic preparations that contain the inhibitor and the ameliorant as active ingredients are provided. A tyrosinase activity inhibitor and an ameliorant for facial blood flow that contain anthocyan obtained by concentration or extraction of plant material, and medicinal compositions, food compositions, and cosmetic preparations that have an inhibitory action on tyrosinase activity and ameliorating action on facial blood flow are provided.

3 Claims, 1 Drawing Sheet

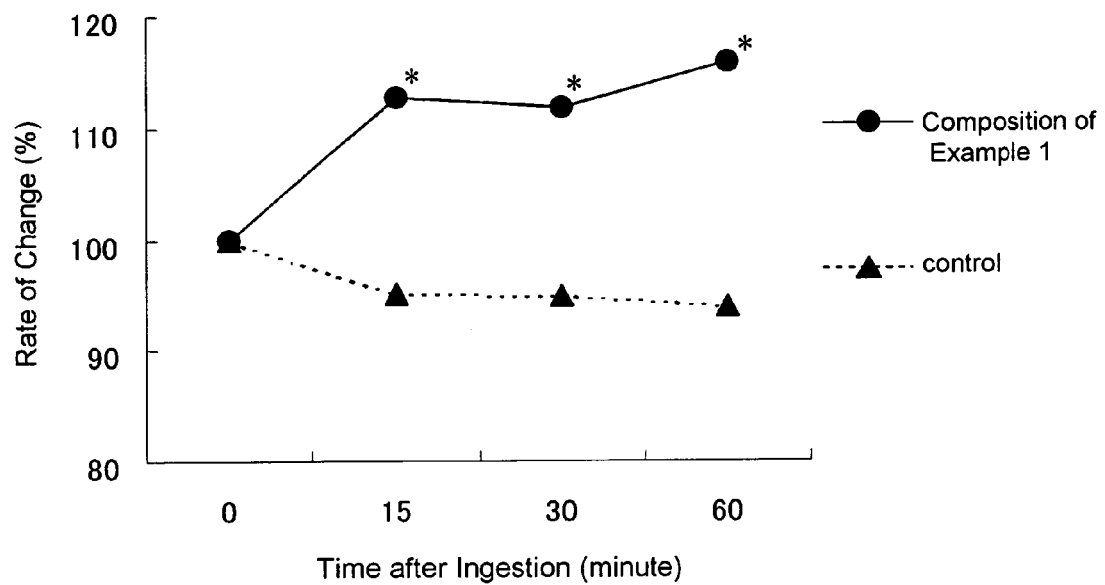

US 7,863,248 B2

TYROSINASE ACTIVITY INHIBITOR AND AMELIORANT FOR FACIAL BLOOD FLOW

CROSS-REFERENCE TO RELATED APPLICATIONS

This application is a U.S. national phase application of International Application No. PCT/JP2004/015470, filed Oct. 20, 2004, which claims priority from Japanese patent application No. 2003-371080, filed Oct. 30, 2003.

TECHNICAL FIELD

The present invention relates to a tyrosinase activity inhibitor and to an ameliorant for facial blood flow that contain anthocyan, and to medicinal compositions, food compositions, and cosmetic preparations that contain anthocyan as an active ingredient. The composition of the present invention has an inhibitory effect on tyrosinase activity and an ameliorating effect on facial blood flow, and is excellent in terms of safety.

BACKGROUND ART

For women, spots, freckles, and dark undereye circles are significant cosmetic concerns, as are as wrinkles and sagging. Skin color is determined depending on four types of pigments (melanin, oxygenated hemoglobin, reduced hemoglobin, and carotene) and light-scattering phenomena. Particularly, in the case of melanin, signal transduction pathway for melanin production in an epidermal pigment cell (melanocyte) is activated as a result of abnormal hormone secretion, ultraviolet stimulation, inflammatory stimulation, or the like, resulting in production of tyrosinase that is a main enzyme that produces melanin and excessive expression of tyrosinase activity. Accordingly, excessive melanin pigmentation results in creation of spots and freckles. As a means for preventing such spots and freckles, a substance that inhibits the activity of tyrosinase, which is a conventional melanin-producing main enzyme, is used. Hitherto, many types of melanin-production inhibitors such as vitamin C derivatives, placenta extract, arbutin, kojic acid, ellagic acid, tannic acid, glycyrrhiza extract, and placenta extract have been developed [Maeda, K: FRAGRANCE JOURNAL, 1997, September issue: 10-18] (Non-Patent Document 1). In addition, a whitening item that contains cranberry-derived caffeic acid glycoside has peen reported in JP Patent Publication (Kokai) No. 5-201846 A 1993 (Patent Document 1). However, under the present circumstances, sufficient effects have not been obtained therefrom.

Meanwhile, in recent years, the use of kojic acid and the like in food has been banned because of a problem in terms of edibility of such substance when it is contained in food. Only limited substances such as vitamin C have been used in practice. In addition, effects obtained from such substances have still been insufficient.

In addition, poor facial blood flow is one cause of dark undereye circles. It has been known that blue or black undereye circles appear due to increase in the amount of reduced hemoglobin. Also, poor facial blood flow is one cause of spots and freckles. However, no substance that has a blood flow ameliorating effect as a mechanism of action or a function of improving spots and freckles has yet been found.

Similarly, it has been known that dullness is created by the following two factors: blackening of the face due to increase in the amount of reduced hemoglobin resulting from poor facial blood flow; and production of black melanin in relation to tyrosinase activity.

Under such circumstances, a desired composition is required to have an inhibitory effect on tyrosinase activity and an ameliorating effect on facial blood flow, which are expressed at important sites of action in the treatment of spots, freckles, dark undereye circles, and dullness, and to be sufficient in view of safety, taste, food texture, and cost.

[Patent Document 1] JP Patent Publication (Kokai) No. 5-201846 A 1993

[Non-Patent Document 1] Maeda, K: FRAGRANCE JOURNAL, 1997, September issue: 10-18

DISCLOSURE OF THE INVENTION

As described above, ascorbic acids, hydroquinone derivative, kojic acid, placenta extract, and the like have weak inhibitory effects on tyrosinase activity, and besides, it cannot be said that they are sufficient in terms of safety. Thus, in recent years, various types of active ingredients contained in plant extracts have been gaining attention. A variety of actions, such as antitumor actions of such substance, have been reported, in addition to the antioxidative action of polyphenol contained in a number of plants. *Rosa laevigata* and Rose Fruit have been known as plants classified as *Rosaceae Rosa*. Extracts of such plants have inhibitory effects on tyrosinase activity. However, the inhibitory effects on tyrosinase activity obtained from them have been insufficient. Needless to say, no ameliorating action on blood flow has been found in such plants.

On the other hand, examples of substances having ameliorating action on blood flow include vitamin E, chitosan, ginkgo leaves, saffron extract, and the like. However, it has been difficult for these substances to inhibit melanin production. As a result of intensive studies in view of above circumstances, inventors of the present invention have found that anthocyan has an inhibitory effect on tyrosinase activity and an ameliorating effect on facial blood flow. This has led to the completion of the present invention. In addition, it has been proved that the ameliorating effect on facial blood flow obtained from anthocyan is expressed within 15 minutes after oral ingestion of anthocyan, and thus an instantaneous effect of anthocyan is provided.

It is an objective of the present invention to provide a tyrosinase activity inhibitor or an ameliorant for facial blood flow that contains anthocyan, and a medicinal composition, food composition, or cosmetic preparation that contains anthocyan as an active ingredient. The composition of the present invention has an inhibitory effect on tyrosinase activity and an ameliorating effect on facial blood flow, and is excellent in terms of safety.

As a result of intensive studies to attain the above objective, the inventors of the present invention have found that anthocyan has an inhibitory effect on tyrosinase activity and an ameliorating effect on facial blood flow, and that such effects of anthocyan are synergistically expressed upon ingestion of medicaments, foods, and the like that contains anthocyan. This has led to the completion of the present invention.

Preferably, the compound of the present invention is anthocyan, which is a type of polyphenol. A compound having the skeletal structure shown in the following structural formula is generally termed anthocyan. Particularly, such a compound having only aglycon and such a compound to which a saccharide as glycoside binds are referred to as anthocyanidin and anthocyanin, respectively. As described below, anthocyanidin can be referred to as delphinidin, cyanidin, malvidin, pelargonidin, peonidin, or petunidin depending on the type of side chain. For instance, anthocyanidin to which glucose as glycoside binds can be referred to as anthocyanidin glucoside:

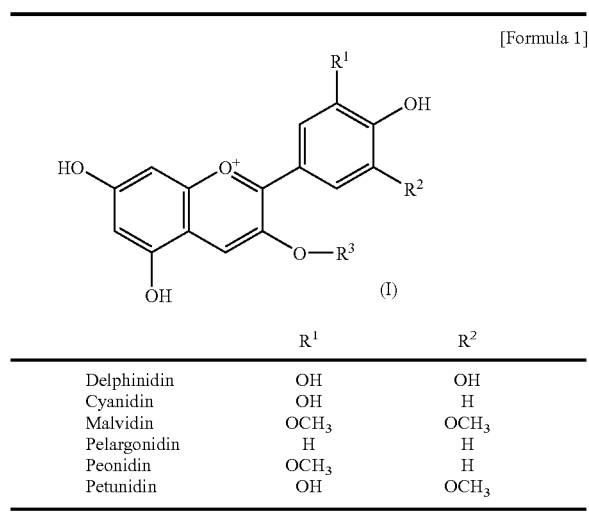

[Formula 1]

|  | R¹ | R² |
| --- | --- | --- |
| Delphinidin | OH | OH |
| Cyanidin | OH | H |
| Malvidin | OCH$_3$ | OCH$_3$ |
| Pelargonidin | H | H |
| Peonidin | OCH$_3$ | H |
| Petunidin | OH | OCH$_3$ |

[wherein, R$^1$ and R$^2$ denote the same member or different members selected from a group consisting of a hydrogen atom, a hydroxyl group, and a methoxy group; R$^3$ denotes a hydrogen atom or Gly; and Gly denotes a saccharide group such as glucose, rutinose, arabinose, galactose, or sophorose].

Anthocyan widely exists in nature. Anthocyan has been used as a natural pigment in food, and has been used extensively in medicaments, quasi-drugs, and cosmetics in Europe due to its functionality. For instance, anthocyan has been used as an epulotic agent as described in JP Patent Publication (Kokoku) No. 59-53883 B 1984, and blueberry-derived anthocyan has been found to have pharmacological properties that are valuable in terms of treatment of peripheral vessels as described in JP Patent Publication (Kokai) No. 3-81220 A 1991. Recently, in Japan, the functionality of anthocyan has been gaining attention in terms of non-pigment usage.

Particularly, the inventors have found that delphinidin-3-glucoside (hereafter abbreviated as D3G), delphinidin-3-rutinoside (hereafter abbreviated as D3R), and cyanidin-3-glucoside (hereafter abbreviated as C3G) have tyrosinase inhibitory activity at the same level as that found in comparative drugs such as kojic acid, arbutin, and the like. Thus, they are effective in terms of skin-beautifying effects and treatment and prevention of erythema, black spots, and the like. At the same time, the inventors have found that the anthocyan compound of the present invention has the effect of increasing the volume of facial blood flow within 15 minutes after oral ingestion of the compound.

Thus, it is an objective of the present invention to provide a tyrosinase activity inhibitor or an ameliorant for facial blood flow that contains anthocyan and a medicinal composition, food composition, or cosmetic preparation that contains anthocyan as an active ingredient.

This specification includes part or all of the contents as disclosed in the specification and/or drawings of Japanese Patent Application No. 2003-371080, which is a priority document of the present application.

As described above in detail, according to the present invention, a highly safe medicinal composition, food composition, or cosmetic preparation that is excellent in terms of having an inhibitory effect on tyrosinase activity and an ameliorating effect on facial blood flow, is provided.

BRIEF DESCRIPTION OF THE DRAWINGS

FIG. 1 shows changes in the volume of blood flow after administration of the composition of the present invention.

BEST METHOD FOR CARRYING OUT THE INVENTION

The present invention will be hereafter described in detail. Since a medicinal composition, food composition, or cosmetic preparation that contains anthocyan of the present invention has an inhibitory effect on tyrosinase activity and/or an ameliorating effect on facial blood flow, an effective skin-beautifying effect can be obtained using such substances.

As anthocyan used in the present invention, anthocyan extracted from an anthocyan-rich substance can be used. Examples thereof include purple sweet potato, red cabbage, elderberry, grape juice or grape skin, grape skin, purple corn, red radish, perilla, red rice, cassis, cowberry, gooseberry, cranberry, salmonberry, "suimu" blueberry, strawberry, dark sweet cherry, cherry, hibiscus, huckleberry, blackberry, blueberry, plum, whortleberry, boysenberry, mulberry, purple potato, purple yam, raspberry, red currant, and loganberry. For instance, anthocyan used in the present invention may be crystallized forms of anthocyan such as delphinidin-3-glucoside, delphinidin-3-rutinoside, or cyanidin-3-glucoside described in the application (WO02/22847) filed by the inventors. As an example thereof, a compound extracted from a plant, which has been disclosed by the inventors of the present application (WO01/01798), can be used. Since the cost of the raw material of anthocyan is high, it is preferable that anthocyan be extracted from berries among the above. Crystallized forms of anthocyanin such as delphinidin-3-glucoside, cyanidin-3-glucoside and rutinoside disclosed by the inventors of the present invention (WO02/22847) are also desirable. Anthocyanin and crystals thereof can be obtained in accordance with the descriptions of WO01/01798 and WO02/22847. The general formula for anthocyan is as described above. As the aglycon part thereof, any one of delphinidin, cyanidin, malvidin, pelargonidin, peonidin, or petunidin may be used; however, delphinidin or cyanidin is preferable. As the saccharide part thereof, any one of glucose, rutinose, arabinose, galactose, or sophorose may be used, or a similar substance may be used. Also, anthocyan to which no saccharide binds may be used. In addition, a food composition containing anthocyan described in the application filed by the inventors of the present invention (WO01/01798) may be used as the composition of the present invention.

In the past studies, such compound was found to be non-toxic and to exist in the blood or in the skin of a subject after oral administration thereof to a subject. Thus, the compound can be administered orally or parenterally.

Desirably, the raw material of the compound is plant material as described above. Preferably, fresh fruits, dried fruits, crushed fruits, puree, fresh fruit juice, concentrated fruit juice, or the like is used. In addition, preferably, a method for producing anthocyan involves membrane concentration or extraction of the above raw material. Upon membrane concentration, prior compression filtration is necessary. Before this, preferably, deactivation treatment on pectin is carried out so as to reduce the viscosity of filtrated matter. Upon extraction, anthocyan can be obtained via extraction using water; polyalcohol such as 1,3-butylene glycol, propylene glycol, glycerin, or diglycerin; lower alcohol such as ethanol, isopropyl alcohol, or propyl alcohol; solvents such as acetone; or mixed solvents thereof. Preferably, water, polyalcohol, lower alcohol, and mixed solvents thereof, and further preferably warm water or hot water, are used. Examples of the form of the thus obtained extract include a solvent-containing extract, a solvent-free extract, and the like. However, in the present invention, as anthocyan, a concentrate of fruit juice obtained by membrane concentration is preferably used in terms of the ease of production of raw material and cost-effectiveness. A higher anthocyan concentration desirably results in the easier processing of the raw material. Anthocyan in the form of fresh fruit, squeezed fruit juice, or dried fruit can be used; however, anthocyan in a powdered form or as a solvent extract is preferably used in view of usability and pharmaceutical manufacturability. In terms of the degree of purification of the anthocyan concentrate or extract used in the present invention, a purified product containing anthocyan at a high content is desirable. Preferably, the purified product contains at least 1% or more anthocyan, and more preferably 5% or more anthocyan. Anthocyan is characterized by the high skin safety and the low cytotoxicity. The thus obtained anthocyan-containing composition is highly safe, and is excellent in terms of its inhibitory effect on tyrosinase activity and its ameliorating effect on facial blood flow.

When a medicinal composition containing, as an active ingredient, anthocyan of the present invention is used, the composition contains approximately 0.1% to 50% anthocyan by weight, and preferably by approximately 0.1% to 20% anthocyan by weight, although the content of anthocyan differs depending on the dosage form of the composition. The dose of anthocyan is appropriately determined in response to individual cases based on the consideration of the age, the weight, the sex, the presence or absence of disease, and the degree of symptoms of a patient. In general, anthocyan is administered to an adult in an amount of 1 to 1000 mg and preferably 1 to 200 mg per day at one time or divided it into two or more doses.

The composition of the present invention has tyrosinase inhibitory activity. Since tyrosinase is a main enzyme that produces melanin, the composition can suppress melanin production and can also prevent or alleviate spots and freckles created on the skin. In addition, the composition of the present invention has an ameliorating action on facial blood flow. Thus, the composition ameliorates facial blood flow so as to prevent or alleviate dark undereye circles and dullness as a result of poor blood flow.

In addition to the compound of the present invention, preferably, a whitening agent that has been conventionally known to have a skin-beautifying effect is used in combination therewith. Thus, a synergistically enhanced skin-beautifying effect can be obtained, compared with the effect obtained from the use of the compound alone. Examples of such whitening agent used in combination include arbutin, ellagic acid, placenta extract, vitamin C and derivatives thereof, rcinol, glutathione, linolic acid, linolenic acid, lactic acid, tranexamic acid, biphenyl compound, calcium pantetheine-S-sulfonate, sulfur, oil-soluble *glycyrrhiza* extract (glabridin), raspberry ketone glucoside, *uva ursi* extract, *glycyrrhiza* extract, acelora extract, almond extract, aloe extract, *ginkgo* extract, *Bistorta major* extract, rose fruit extract, *Scittellaria* root extract, *Coptis japonica* extract, *Hypericum erectum* extract, white nettle (*Lamium album*) extract, seaweed extract, chamomile extract, *Pueraria* root (kudzu) extract, phellodendron extract, gardenia extract, clara (*Sophora* root) extract, chlorella extract, brown sugar extract, mulberry (mulberry bark) extract, gentian extract, tea extract, *Gallae Rhois* (*Gallae chinensis*) extract, wheat extract, rice germ oil, wheat germ extract, rice bran extract, *Asiasarum* root extract, *Gardenia jasminoides* extract, zanthoxylum extract, perilla extract, peony extract, honeysuckle extract, sage extract, *Cnidium rhizome* extract, soybean extract, green tea extract (leaves or fruit bodies), *Angelica acutiloba* extract, pot marigold (*Calendula officinalis*) extract, peach kernel extract, houttuynia extract, garlic extract, hamamelis extract, loquat extract, safflower extract, tree peony extract, hoelen extract, marronnier extract, melissa extract, coix seed (*Coix lachryma-jobi*) extract, saxifraga extract, *Sanguisorba officinalis* extract, mugwort extract, *Pyracantha fortuneana* extract, and hibiscus extract. Among them, the following substances or extracts that are rich in general versatility and stability thereof are preferable: forms of vitamin C such as ascorbic acid, sodium ascorbate, ascorbyl phosphate magnesium, ascorbyl stearate, ascorbyl palmitate, ascorbyl dipalmitate, ascorbic acid clucoside, and the like, and derivatives thereof; lactic acid; placenta extract; oil-soluble *glycyrrhiza* extract; aloe extract; honeysuckle extract; hibiscus extract; coix seed extract; green tea extract; and saxifraga extract. Among them, vitamin C, derivatives thereof, and placenta extract are particularly preferable.

Combined with use of an antiinflammatory agent, the composition of the present invention achieves the effect of further improving and preventing pigmentation such as spots, freckles, dullness, or the like caused by ultraviolet rays. Thus, preferably, an antiinflammatory agent is used in combination with the composition of the present invention. The antiinflammatory agent used is one or two members selected from the group consisting of: glyrrhetinic acid and glycyrrhetinic acid, salts thereof, and esters thereof; *glycyrrhiza* extract; turmeric extract; *Scutellaria* root extract; barley extract, peony extract; birch sap; peach leaf extract; allantoin; ϵ-aminocaproic acid; indomethacin; guaiazulene; lysozyme hydrochloride; hydrocortisone; and panthenol and derivatives thereof.

The aforementioned medicinal ingredients are not particularly limited as long as they have been conventionally used in medicaments, quasi-drugs, cosmetics, hygienic goods, miscellaneous goods, and the like. Among them, those having a tyrosinase inhibitory effect or an antiinflammatory effect can be used as another example of the tyrosinase activity inhibitor of the present invention or an antiinflammatory agent. Examples of such medicinal ingredients include *Angelica keiskei* extract, avocado extract, sweet hydrangea leaf extract, althea extract, arnica extract, apricot extract, fennel extract, echinacea leaf extract, *Phellodendron* bark extract, watercress extract, orange extract, dried seaweed, hydrolyzed elastin, hydrolyzed silk, chamomile extract, carrot extract, *Artemisia capillaris* extract, karkade extract, kiwi fruit extract, cinchona extract, cucumber extract, guanosine, *Sasa veitchii* extract, walnut extract, grapefruit extract, clematis extract, yeast extract, burdock extract, comfrey extract, collagen, *Bupleurum chinense* (*Bupleurum scorzonerifolium*) extract, umbilical cord extract, salvia extract, soapwort extract, sasa extract, *Crataegus cuneata* extract, shiitake mushroom extract, *Rehmannia* root extract, *Lithospermi radix* extract, *Tilia japonica* extract, spiraea (*Filipendula multijuga*) extract, *Acorus calamus* root extract, birch extract, horsetail (*Equisetum arvense*) extract, English ivy (*Hedera helix* L.) extract, hawthorn extract, elderberry (*Sambucus nigra*) extract, yarrow (*Achillea millefolium*) extract, *Mentha piperita* extract, mallow extract, *Swertia japonica* extract, *Zizyphi fructus* extract, thyme extract, clove extract, *Imperata cylindrica* extract, *Citrus unshiu* peel (*Aurantii nobilis pericarpium*) extract, *Picea jezoensis* var. *hondoensis* extract, tomato extract, fermented soybean (natto) extract, carrot extract, rose (*Rosa multiflora*) extract, *Ophiopogonis* tuber extract, parsley extract, honey, parietaria extract, *Isodon japonicus* extract, bisabolol, coltsfoot extract, butterbur sprout extract, poria extract, butcherbroom extract, grape extract, propolis, luffa extract, peppermint extract, linden extract, hop extract, pine extract, Japanese skunk cabbage (*Lysichiton camtschatense*) extract, *Sapindus mukurossi* extract, cornflower (*Centaurea cyanus*) extract, eucalyptus extract, *Citrus junos* extract, lavender extract, apple extract, lettuce extract, lemon extract, astragalus (*Astragalus sinicus*) extract, rose extract, rosemary extract, roman chamomile extract, and royal jelly extract.

Examples thereof also include mucopolysaccharides such as sodium hyaluronate and sodium chondroitin sulfate; biopolymers such as deoxyribonucleic acid, collagen, elastin, chitin, chitosan, and hydrolyzed eggshell membrane; moisturizing ingredients such as amino acid, urea, sodium pyrrolidone carboxylic acid, betaine, whey, and trimethylglycine; oily ingredients such as sphingolipid, ceramide, cholesterol, cholesterol derivative, and phospholipid; vitamins such as biotin, nicotinic acid amide, and vitamins A, B2, B6, D, and K; active ingredients such as diisopropylamine dichloroacetate and 4-(aminomethyl)cyclohexanecarboxylic acid; wound-healing agents such as retinol and retinol derivative; cepharanthin; capsicum tincture; hinokitiol; iodized garlic extract; pyridoxine hydrochloride; nicotinic acid; nicotinic acid derivative; isopropyl methyl phenol; estradiol; ethinyl estradiol; capronium chloride; benzalkonium chloride; diphenhydramine hydrochloride; takanal; camphor; salicylic acid; nonylic acid vanillyl amide; nonanoic acid vanillyl amide; piroxolamine; pentadecane acid glyceryl; 1-menthol; pyrrolidone carboxylate of menthol; mononitroguaiacol; resorcin; γ-aminobutyric acid; benzethonium chloride; mexiletine hydrochloride; auxin; estrogen; cantharis tincture; ciclosporin; hydrocortisone; polyoxyethylene sorbitan monostearate; peppermint oil; analgesics; and antibiotics.

The composition of the present invention containing a tyrosinase inhibitor and an ameliorant for facial blood flow as food material can be used with delphinidin-3-glucoside, delphinidin-3-rutinoside, and cyanidin-3-glucoside described in the application filed by the inventors (WO02/22847) and food compositions or beverages and foods containing anthocyan described in the application filed by the inventors (WO01/01798). Thus, it is possible to produce functional foods that prevent or ameliorate spots, freckles, dark undereye circles, and dullness. The composition of the present invention can be used for producing foods for specified health use suitable for prevention or amelioration of spots and freckles. More specifically, the composition of the present invention can be added to foods in various forms such as solid foods, jelly-like foods, liquid foods, and capsule foods. Herein, examples of solid foods include bread dough; dough for rice crackers, biscuits, cookies, and the like; noodles such as buckwheat noodles and wheat noodles; fish products such as steamed fish paste and fish sausage; livestock meat products such as ham and sausage; and powdered milk. In addition, examples of jelly-like foods include fruit jellies, coffee jellies, and the like. Further, examples of liquid foods include green tea, coffee, tea, fermented milk, lactic acid bacteria beverages, and the like. Examples of capsule foods include hard capsules, soft capsules, and the like.

When the composition of the present invention is added to foods described above, the composition of the present invention can be mixed therein in a manner such that the content of the compound is 0.01% to 10% by weight of the total weight of the foods. The intake at a level at which an anticipated effect can be obtained is appropriately determined in response to individual cases based on the consideration of the age, the weight, the sex, the degree of symptoms, and the like of a subject. In general, anthocyan is administered to an adult in an amount of 1 to 1000 mg and preferably 10 to 200 mg per day at one time or divided into two or more doses.

In addition, according to the present invention, tyrosinase inhibitory activity and an ameliorating effect on facial blood flow are obtained. Thus, it is expected that a skin-beautifying effect can be obtained using the composition of the present invention. Herein, the term "skin-beautifying" indicates alleviation or prevention of spots, freckles, dark undereye circles, and dullness on the face. The aforementioned medicinal composition, food composition, or cosmetic preparation that contains anthocyan can be applied to a subject who has at least one symptom selected from the group consisting of symptoms comprising spots, freckles, dark undereye circles, and dullness on the face.

EXAMPLES

The present invention will be hereafter described in detail by referring to examples. However, the scope of the invention is not limited by these examples.

Example 1

Preparation of an Anthocyan-Containing Composition 3 kg of commercially available concentrated juice of cassis (anthocyan purity: 2.8% of the solid content) was diluted with water so as to prepare the diluted juice of cassis at a concentration of Bx. 10 (solid concentration: 10%). The obtained diluted juice was filtered using filter paper so as to remove foreign bodies therefrom. Then, membrane separation was conducted using an apparatus to which a negatively charged reverse osmosis membrane (NF membrane) (NTR-7410; Nitto Denko Corp.) was applied. The separation was repeatedly performed until circulation of the obtained concentrated solution was stopped. Thereafter, water was again added to the solution such that the solution was diluted, followed by subsequent separation in a continuous manner. When circulation of the concentrated solution was stopped, separation was terminated. The concentrated solution was subjected to spray-drying, whereby an anthocyan-rich composition in a powdered form was obtained. The anthocyan purity of the composition was 14.1% of the solid content.

Example 2

Preparation of Anthocyanin Crystals

Further, anthocyanin crystals were prepared from the composition of the present invention.

40 g of powdered anthocyanin (ingredient breakdown of anthocyanin: D3G: 12.5%; D3R: 47.9%; C3G: 4.1%; and C3R: 35.5%) obtained in accordance with the method described in Example 1 was fractionated using a 9% acetonitrile solution containing 0.1% TFA with an ODS silica gel column.

Accordingly, D3G fraction (1.51 g), C3G fraction (0.98 g), C3R fraction (162 mg), and D3R fraction (231 mg) were obtained.

The thus obtained concentrate was dissolved in a 5% hydrogen chloride/methanol solution. Then, the resulting solution was allowed to stand at 5° C. for 24 hours, whereby anthocyanin therein was crystallized. Accordingly, crystallized D3G hydrochloride (1.06 g), crystallized C3G hydrochloride (0.59 g), crystallized C3R hydrochloride (58 mg), and crystallized D3R hydrochloride (88 mg) were prepared.

Experimental Example 1

Experimentation Regarding Tyrosinase Activity Inhibition

As test substances, the composition prepared in Example 1 and four types of anthocyanin crystal prepared in Example 2 were used.

To a 96-well plate, 40 μl of mushroom-derived tyrosinase (125 unit/ml; dissolved in a 67 mmol/l phosphate buffer solution; Sigma), 120 μl of 3,4-dihydroxyphenylalanine that serves as a substrate (L-dopa; 5 mmol/l; dissolved in a 67 mmol/l phosphate buffer solution; Sigma), and 40 μl of an inhibitor solution were added. The plate was allowed to stand for 37° C. for 30 minutes. Then, the amount of dopachrome produced was determined by absorbance at 490 nm. Tyrosinase inhibitory activity was expressed as an inhibitory rate obtained by the following equation:

$$\text{Inhibitory Rate (\%)} = [(A-B)-(C-D)]/(A-B) \times 100$$

A: absorbance at 490 nm of a control solution
B: absorbance at 490 nm of a control solution (blank solution)
C: absorbance at 490 nm of an anthocyanin solution
D: absorbance at 490 nm of an anthocyanin solution (blank solution).

The results are shown in table 1. The composition obtained in Example 1 was found to have higher tyrosinase inhibitory activity than arbutin.

In addition, the anthocyanin crystals obtained in Example 2 were found to have higher tyrosinase inhibitory activity than L-cysteine, kojic acid, or glutathione.

TABLE 1

| Inhibitor | Concentration (mg/ml) | Concentration (mM) | Inhibitory Rate (%) |
|---|---|---|---|
| Cassis-Anthocyanin Composition (Example 1) | 2 | | 64.8 |
| D3G (Example 2) | 0.102 | 0.2 | 67.5 |
| D3R (Example 2) | 0.135 | 0.2 | 70.1 |
| C3G (Example 2) | 0.099 | 0.2 | 45.0 |
| Arbutin | 2.7 | 10 | 10.4 |
| Kojic Acid | — | 0.2 | 34.7 |
| L-Cysteine | — | 0.2 | 29.8 |
| Glutathione | — | 0.2 | 13.2 |

Experimental Example 2

Experimentation Regarding Facial Blood Flow Amelioration

As a test substance, the composition prepared in Example 1 was used.

The volume of facial blood flow was determined using a laser Doppler blood flowmeter with a probe placed on the cheek of a subject. Subjects were 6 males and females between 25 years old and 38 years old. First, they were acclimated under room temperature conditions at 23±1° C. and a humidity of 45±5% for 30 minutes. Thereafter, they were subjected to measurement of the volume of facial blood flow before ingestion of the composition. Then, they ingested 465 mg of the composition of Example 1 or sucrose as a control in an amount such that the amount of calories contained therein was equivalent to that of the compound. The volume of facial blood flow of each subject was measured 15 minutes, 30 minutes, and 60 minutes after ingestion.

The results are shown in FIG. 1. It is understood that, after ingestion of the composition of Example 1, the volume of blood flow in the cheek started to increase 15 minutes after ingestion, resulting in improvement of the volume of facial blood flow due to the instantaneous effect of the composition. Therefore, it can be expected that ingestion of the composition of Example 1 would result in the improvement of spots, freckles, dark undereye circles, dullness, and the like.

All publications, patents, and patent applications cited herein are incorporated herein by reference in their entirety.

The invention claimed is:

1. A method of inhibiting tyrosinase activity in a subject in need of alleviating spots or freckles created on the skin, which comprises ingesting a composition comprising an effective amount of anthocyan for alleviating spots and freckles on the skin to the subject.

2. The method according to claim 1, wherein anthocyan is glycoside of delphinidin and/or glycoside of cyanidin.

3. The method according to claim 1, wherein the composition comprises 0.1% to 50% by weight of anthocyan.

* * * * *